(12) United States Patent
Baars et al.

(10) Patent No.: US 8,304,378 B2
(45) Date of Patent: Nov. 6, 2012

(54) CLEANING AND DISINFECTANT COMPOSITIONS

(75) Inventors: Evert Pieter ids Baars, Wijk bij Duurstede (NL); Peter Benjamins, Nieuwegein (NL); Kathleen J. Bixler, Racine, WI (US); Pablo M. Hernandez, Waukegan, IL (US); Ryan E. Kron, Racine, WI (US); Peter Y. Mizuki, Racine, WI (US); Ying J. Zhou, Greendale, WI (US)

(73) Assignee: Diversey, Inc., Sturtevant, WI (US)

( * ) Notice: Subject to any disclaimer, the term of this patent is extended or adjusted under 35 U.S.C. 154(b) by 897 days.

(21) Appl. No.: 11/248,113

(22) Filed: Oct. 12, 2005

(65) Prior Publication Data

US 2006/0100122 A1      May 11, 2006

Related U.S. Application Data

(60) Provisional application No. 60/522,775, filed on Nov. 5, 2004.

(51) Int. Cl.
    *C11D 3/00*      (2006.01)
(52) U.S. Cl. ........................................................ 510/375
(58) Field of Classification Search .................... None
    See application file for complete search history.

(56) References Cited

U.S. PATENT DOCUMENTS

| | | | | |
|---|---|---|---|---|
| 3,194,768 A | | 7/1965 | Lindner et al. | 252/186 |
| 4,164,477 A | * | 8/1979 | Whitley | 510/199 |
| 4,304,762 A | * | 12/1981 | Leigh | 423/272 |
| 4,919,838 A | * | 4/1990 | Tibbetts et al. | 510/120 |
| 6,127,330 A | * | 10/2000 | Bonett | 510/370 |
| 6,183,763 B1 | * | 2/2001 | Beerse et al. | 424/404 |
| 6,514,924 B1 | | 2/2003 | Van Hauwermeiren et al. | 510/284 |
| 6,541,436 B1 | | 4/2003 | Arvanitidou et al. | 510/235 |
| 6,660,711 B1 | | 12/2003 | Price et al. | 510/499 |
| 2003/0047539 A1 | * | 3/2003 | Ma et al. | 216/89 |
| 2003/0136942 A1 | | 7/2003 | Smith et al. | 252/186.26 |
| 2003/0203831 A1 | * | 10/2003 | Wisniewski et al. | 510/438 |

FOREIGN PATENT DOCUMENTS

| | | |
|---|---|---|
| DE | 100 32 589 A 1 | 1/2002 |
| JP | 10251689 | 9/1998 |
| WO | WO 03/080782 A 1 | 10/2003 |

\* cited by examiner

*Primary Examiner* — Brian Gulledge
(74) *Attorney, Agent, or Firm* — Michael Best & Friedrich LLP

(57) ABSTRACT

Cleaning and disinfectant compositions are provided particularly for use with hard surfaces. The compositions include hydrogen peroxide and an acid or salt thereof which is resistant to oxidation other than phosphorous based acids. Replacement of phosphorous based acids with acids of the invention results in improved hydrogen peroxide stability while maintaining or increasing the efficacy of cleaning and antimicrobial activity of the compositions. Typically, acids of the invention include substituted or unsubstituted carboxylic acids such as $R^4-C(R^2)(R^3)-R^1-COOH$. Inventive compositions may further include surfactants, a chelating agent or sequestrant, a water soluble or water dispersible solvent, corrosion inhibitors and other adjuvants well known to those skilled in the art. There are further provided methods of use and methods of preparing inventive compositions.

17 Claims, No Drawings

CLEANING AND DISINFECTANT COMPOSITIONS

CROSS-REFERENCE TO RELATED APPLICATION

This application claims priority based on U.S. Provisional Application No. 60/522,775 filed Nov. 5, 2004.

STATEMENT REGARDING FEDERALLY SPONSORED RESEARCH

Not applicable.

FIELD OF THE INVENTION

The present invention relates to cleaning and disinfectant compositions for use on hard surfaces. In particular, it relates to hydrogen peroxide solutions with improved stability and antimicrobial properties and methods of use thereof.

BACKGROUND OF THE INVENTION

Disinfectants incorporating hydrogen peroxide are attractive because hydrogen peroxide displays broad spectrum antimicrobial activity and because it decomposes into innocuous products, i.e., water and oxygen. Broad spectrum antimicrobial activity is important in situations where harmful organisms are present, but their identity is not known. Drawbacks to the use of hydrogen peroxide include the inherent instability of hydrogen peroxide solutions and the length of time required for hydrogen peroxide to disinfect a surface to which it had been applied. For example, stabilizers must be added to hydrogen peroxide solutions if they are to be stored for any length of time. Also, it can take 30 minutes or more after application of such solutions to disinfect a treated surface. Recently, it has been disclosed that a combination of a phosphorous based acid and an anionic surfactant can stabilize and increase the activity of hydrogen peroxide solutions. Nevertheless, hydrogen peroxide solutions with improved cleaning and disinfecting activity would be highly desirable. The present invention is therefore directed to improving the efficacy of hydrogen peroxide based solutions.

SUMMARY OF THE INVENTION

In accordance with one aspect of the present invention, there are provided aqueous cleaning and disinfecting compositions which include hydrogen peroxide and an acid or salt thereof which is resistant to oxidation, other than a phosphorous containing acid. It has unexpectedly been discovered that in hydrogen peroxide based disinfectants replacement of phosphorous containing acids by acids that are resistant to oxidation by hydrogen peroxide enhances the stability of the hydrogen peroxide while at the same time maintaining or increasing cleaning and antimicrobial efficacy. Moreover, the present compositions are highly effective, both as concentrated solutions, or at various dilutions. Hence, the present compositions are especially well suited for use as an all purpose cleaner and disinfectant for hard surfaces. For example, inventive compositions are low streaking and leave little residue on glass surfaces such as mirrors. They may be used to maintain grout and fixtures from iron and hard water stains and can whiten grout. The present cleaning and disinfectant compositions can also be formulated for safe use on metal surfaces and fixtures such as stainless steel and aluminum surfaces and fixtures.

According to a second aspect of the invention, there are provided methods of cleaning and disinfecting a surface which include the step of applying to the surface a composition as described herein. Inventive compositions may be used as is or diluted with water prior to application to the surface.

In yet a further aspect of the invention, there are provided methods of preparing the cleaning and disinfecting compositions of the invention. The methods include the step of combining the hydrogen peroxide and the acid resistant to oxidation.

DETAILED DESCRIPTION OF THE INVENTION

In one aspect, the present invention provides a composition for use in cleaning and disinfecting fabric, synthetic fibers, semi-hard and hard surfaces such as tile, glass, metal, porcelain and the like. The composition includes hydrogen peroxide and an acid or salt thereof which is resistant to oxidation. Acids contemplated for use in the present invention do not include phosphoric. As employed herein, an acid which is resistant to oxidation exhibits less than or equal to 30 or 20 weight % oxidation by measurement of stability after thirty days exposure to no more than 30 weight percent (wt %) aqueous hydrogen peroxide and no more than 2.0 wt % N chelating agent, of the total composition at 50° C. Acids which exhibit less than or equal to 20 mole % oxidation under the above conditions are particularly suitable for use in the present invention.

Acids resistant to oxidation include, for example, certain substituted or unsubstituted carboxylic acids, such as substituted or unsubstituted branched chain alkyl carboxylic acids. For example, carboxylic acids resistant to oxidation include those having the formula $R^4-C(R^2)(R^3)-R^1-COOH$, wherein $R^1$ is absent or is a substituted or unsubstituted alkylene, heteroalkylene, alkenylene, heteroalkenylene, alkynylene, or heteroalkynylene, each having up to 10 carbon atoms; $R^2$ and $R^3$ are each independently substituted or unsubstituted $C_{1-8}$ alkyl; and $R^4$ is substituted or unsubstituted alkyl, alkenyl, alkynyl, heteroalkyl, heteroalkenyl, or heteroalkynyl. Typically, $R^1$ and $R^4$ are each independently substituted or unsubstituted alkylene. Acids for use in compositions of the invention include but are not limited to 2,2-bishydroxymethylpropionic acid, neopentanoic acid, neoheptanoic acid, neooctanoic acid, neononanoic acid, or neodecanoic acid. It will be understood by those of skill in the art that other carboxylic acids (e.g., certain substituted or unsubstituted heterocyclic carboxylic acids such as picolinic acid and salicylic acid) which are resistant to oxidation according to the criteria herein provided are also contemplated for use in compositions of the invention. Typically, the acid resistant to oxidation is present in an amount of from about 0.1 to about 30 wt % of the total weight of the composition. Typically, the acid resistant to oxidation is present in a preferred amount of from about 0.5 to about 10 wt % of the total weight of the composition.

EXAMPLE 1

Hydrogen Peroxide Stability and Efficacy of Various Acids

All the following formulas were made using a base formula with the exclusion of Phosphoric Acid and its place the subsequent acid amount corrected to meet the Total Acid Number of the phosphoric base Formula and water to equal 100%/wt. Stability of the hydrogen peroxide was determined at 50 C for 4 weeks. Microbial Efficacy was conducted on each of the samples via AOAC Sanitizer Suspension Test 960.09 at 1:64 dilution. All test formulations were diluted 1/64 in 400 PPM (as $CaCO_2$) hard water containing 5.0% horse serum. The test material was held at ambient temperature (24° C.) for 60 seconds at which time a 0.1 ml portion of a 24 hr Brain Heart Infusion broth culture of *S. aureus* ATCC 6538 was added to the test solution and mixed. After 5 min at ambient temperature, the test solution was mixed and a 1.1 ml sample withdrawn and placed into 9.9 ml universal neutralizer. A 0.1 ml portion of test organism added to 9.9 ml of standard hard water containing 5% horse serum and enumerated after 5 minutes served as a control.

Universal neutralizer
RT
3 g lecithin
0.5 g fluid thioglycollate broth
1 g histidine
10 ml phosphate buffer
10 ml phosphate buffer 0.25 N
5 g Sodium thiosulphate
30 ml Tween
Bring volume to 1 L with di water The sample was serially diluted in universal neutralizer and the number of surviving organism enumerated by pour plating with Microbial Content Test Agar. A plated were inverted and incubated at 32° C. for 48 hrs. Colonies were counted with the aide of Quebec colony counter and $\log_{10}$ reduction in colony forming units (CFU)/ml compared to CFU/ml of control samples was determined for each formulation.

Results are in the table below.
Base Formula

| Materials | Wt % |
|---|---|
| Deionized Water | 52.46 |
| 1-hydroxyethlene 1,1 Diphosponic Acid (60%) (Dequest 2010) | 8.00 |
| Dodecyl Benzene Sulfonic Acid (97%) (Biosoft S-101) | 5.00 |
| Decyl(sulfophenoxy) benzenesulfonic acid, disodium salt (60%)(Dowfax 10CL) | 5.00 |
| C6-C10 Alcohol ethoxylate 3.5 moles of EO | 1.50 |
| Benzotriazole | 0.10 |
| Propylene Glycol propyl ether | 10.00 |
| Hydrogen Peroxide (50%) | 15.00 |
| Phosporic Acid (85%) | 2.94 |

| Acid | Total Acid Number | Log Reduction | 4 week Peroxide loss (50 C) |
|---|---|---|---|
| Dimethylol Propionic, 6.50% | 77.04 | >6.37 | 19.82% |
| Furoic acid, 5.50% | 77.01 | >6.37 | 52.98% |
| Picolinic acid, 6.00% | 76.99 | >6.37 | 24.50% |
| Isopicolinic acid, 3.00% | 63.12 | 4.73 | 30.94% |
| Neopentanoic, 5.00% | 76.0 | >6.37 | 25.29% |
| Neoheptanoic, 5.60% | 73.04 | >6.37 | 16.62% |
| Neooctanoic, 6.75% | 73.14 | >6.37 | 22.03% |
| Neononanoic, 7.25% | 74.55 | >6.37 | 4.62% |
| Neodecanoic, 8.25% | 75.87 | >6.29 | 11.57% |
| Isonanoic, 6.75% | 75.94 | >6.29 | 23.34% |
| Lactic acid, 5.00% | 72.88 | 5.89 | 53.38% |
| Isovaleric acid, 6.25% | 78.59 | >6.37 | 29.97% |
| 2-ethyl hexanoic, 7.00% | 76.63 | >6.29 | 28.04% |
| Citric 5.50% | 98.14 | 6.12 | 57.90% |
| Glycolic acid, 3.57% | 67.72 | 5.06 | 37.25% |
| Succinic, 4.50% | 92.82 | 5.64 | 36.27% |
| Nonanoic acid | 74.55 | >6.37 | 35.64% |
| Phosphoric acid, 2.94% | 79.7 | >5.56 | <1% |

EXAMPLE 2

Specific Use of Neodecanoic Acid at Various Wt % and it Activity

To the same base in example 1 the following Wt % of Neodecanoic was used and its subsequent microbial efficacy was compared to both nonanoic acid as well as phosphoric acid examples.

| Material | Wt % | Wt % | Wt % | Wt % | Wt % | Wt % | Wt % |
|---|---|---|---|---|---|---|---|
| Deionized Water | 50.64 | 57.45 | 59.21 | 61.21 | 67.21 | 63.21 | 45.65 |
| Phosphoric Acid | 3.33 | 3.33 | | | | | |
| Nonaoic Acid, 96% | | | | | | | 7.25 |
| Neo Nonanoic Acid | | | 3.0 | 3.0 | 3.0 | 2.0 | |
| Propylene Glycol propyl ether | 10.0 | | | | | | 10.0 |
| Ethylene Glycol monobutyl ether | | 5.0 | 8.0 | 6.0 | 3.0 | 5.0 | |
| Hydrogen peroxide 35% | 21.43 | 21.43 | | | | | |
| Hydrogen peroxide, 50% | | | 15.00 | 15.00 | 15.00 | 15.00 | 15.00 |
| Benzotriazole | 0.10 | | | | | | 0.1 |
| Tolyl triazole (Cobratec 35G) | | 0.29 | 0.29 | 0.29 | 0.29 | 0.29 | |
| Alfonic L-610-3.5 | 1.50 | | | | | | |
| Lubrphos LP-700 | | | | 1.50 | 2.0 | 1.5 | 3.0 |
| Lutensol ON 30 | | 1.50 | 1.50 | | | | |
| Dodecyl benzene sulfonic acid (Marlon AS3) | 5.0 | 5.0 | 5.0 | 5.0 | 5.0 | 5.0 | 5.0 |
| 1-hydroxyethylene-1,1 diphosphonic acid Cublen K 60/Dequest 2010 | 8.0 | 8.0 | 8.0 | 8.0 | 8.0 | 8.0 | 8.0 |
| Chelating Agent | | | | | | | 1.0 |

-continued

| Material | Wt % | Wt % | Wt % | Wt % | Wt % | Wt % | Wt % |
|---|---|---|---|---|---|---|---|
| AOAC Use Dilution at 1:32, 5 min. contact, 400 ppm hard water and 5% blood serum *S. aureus* | +0/30 | +4/30* | +0/30 | +1/30 | +1/30 | +1/30 | +0/30 |

*Considered a failure

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl, and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl, norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Typical unsubstituted alkyl groups include straight and branched chain alkyl groups and cyclic alkyl groups having 1 to 20 carbon atoms, and more typical such groups have from 1 to 10 carbon atoms. Even more typical such groups, also known as unsubstituted lower alkyl groups, have from 1 to 5 carbon atoms. Typically, unsubstituted alkyl groups include straight and branched chain alkyl groups having from 1 to 3 carbon atoms and include methyl, ethyl, propyl, and —CH(CH$_3$)$_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in groups such as carbonyls, carboxyls, and esters; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl) (aryl) amine, diarylamine, heterocyclylamine, (alkyl) (heterocyclyl) amine, (aryl) (heterocyclyl) amine, or diheterocyclylamine group.

The term "alkylene" refers to saturated, divalent straight or branched chain hydrocarbyl groups typically having in the range of 1 up to about 20 carbon atoms, and "substituted alkylene" refers to alkylene groups further bearing one or more substituents as set forth above.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The phrase "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon. Typically unsubstituted alkenyl groups have form 2 to 20 carbons, and in some embodiments such groups have from 2 to 10 carbons.

The term "alkenylene" refers to divalent straight or branched chain hydrocarbyl groups having at least one carbon-carbon double bond, and typically having in the range of about 2 up to 20 carbon atoms, and "substituted alkenylene" refers to alkenylene groups further bearing one or more substituents as set forth above.

The phrase "unsubstituted alkynyl" refers to straight and branched chain groups such as those described with respect to unsubstituted alkyl groups as defined above, except that at least one triple bond exists between two carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others. Typically, unsubstituted alkynyl groups have form 2 to 20 carbons, and in some embodiments such groups have from 2 to 10 carbons.

The phrase "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "unsubstituted heteroalkyl" refers to unsubstituted alkyl groups as defined above in which the carbon chain is interrupted by one or more heteroatoms chosen from N, O, and S. Unsubstituted heteroalkyls containing N may have NH or N (unsubstituted alkyl) in the carbon chain. Thus, unsubstituted heteroalkyls include alkoxy, alkoxyalkyl, alkoxyalkoxy, thioether, alkylaminoalkyl, aminoalkyloxy, and other such groups. Typically, unsubstituted heteroalkyl groups contain 1-5 heteroatoms, and more typically 1-3 heteroatoms.

The phrase "substituted heteroalkyl" has the same meaning with respect to unsubstituted heteroalkyl groups that substituted alkyl groups have with respect to unsubstituted alkyl groups.

The phrase "unsubstituted heteroalkylene" refers to a divalent unsubstituted heteroalkyl group as defined above. Thus —$CH_2$—O—$CH_2$— and —$CH_2$—NH—$CH_2CH_2$— are both examples of unsubstituted heteroalkylenes. The phrase "substituted heteroalkylene" refers to a divalent substituted heteroalkyl group as defined above.

The phrase "unsubstituted heteroalkenyl" refers to unsubstituted alkene groups as defined above in which the carbon chain is interrupted by one or more heteroatoms chosen from N, O, and S. Unsubstituted heteroalkenyls containing N may have NH or N (unsubstituted alkyl or alkene) in the carbon chain. The phrase "substituted heteroalkenyl" has the same meaning with respect to unsubstituted heteroalkenyl groups that substituted heteroalkyl groups have with respect to unsubstituted heteroalkyl groups.

The phrase "unsubstituted heteroalkenylene" refers to a divalent unsubstituted heteroalkenyl group as defined above. Thus —$CH_2$—O—CH=CH— is an example of an unsubstituted heteroalkenylene. The phrase "substituted heteroalkenylene" refers to a divalent substituted heteroalkenyl group as defined above.

The phrase "unsubstituted heteroalkynyl" refers to unsubstituted alkynyl groups as defined above in which the carbon chain is interrupted by one or more heteroatoms chosen from N, O, and S. Unsubstituted heteroalkynyls containing N may have NH or N (unsubstituted alkyl, alkene, or alkyne) in the carbon chain. The phrase "substituted heteroalkynyl" has the same meaning with respect to unsubstituted heteroalkynyl groups that substituted heteroalkyl groups have with respect to unsubstituted heteroalkyl groups.

The phrase "unsubstituted heteroalkynylene" refers to a divalent unsubstituted heteroalkynyl group as defined above. Thus —$CH_2$—O—$CH_2$—C≡C— is an example of an unsubstituted heteroalkynylene. The phrase "substituted heteroalkynylene" refers to a divalent substituted heteroalkynyl group as defined above.

EXAMPLE 3

Of a Heteralkyl Acid

The AOAC Use Dilution test was run with 400 ppm hard water and 5% blood serum

| Raw Material | Wt % | Wt % |
|---|---|---|
| Deionized water | 52.46 | 52.85 |
| Phosphoric Acid | 2.94 | |
| Dimethyl propionic acid | | 2.55 |
| 1-hydroxyethylene-1,1 diphosphonic acid (60%) Dequest 2010 | 8.0 | 8.0 |
| Sodium decyl diphenyloxide disulfonate (Dowfax C10L-60%) | 5.0 | 5.0 |
| Dodecylbenzene sulfonic acid (Biosoft S-101) | 5.0 | 5.0 |
| Hydrogen peroxide (50%) | 15.00 | 15.00 |
| C6-C10 Alcohol Ethoxylate (alfonic L610-3.5) | 1.5 | 1.50 |
| Propylene Glycol n-Propyl Ether | 10.00 | 10.0 |
| Benzotriazole | 0.10 | 0.10 |
| % H2O2 Loss after 4 weeks at 50 C | 12.60 | 22.72 |
| AOAC Use Dilution Test at 1:64 S. aueus | +0/30 | +0/30 |
| AOAC Use Dilution Test at 1:64 P. aeruginosa | +0/30 | +0/30 |

Hydrogen peroxide is present as an aqueous solution in inventive compositions. The amount of hydrogen peroxide varies depending on whether the composition is intended as a concentrate or a ready-to-use formulation. The hydrogen peroxide composition may also be used in a concentrated undiluted manner which is particularly useful as a sporicide. For example, the hydrogen peroxide solution may be prepared as a concentrated aqueous solution, at up to about 30 wt % hydrogen peroxide, typically, at up to about 8 wt %, which then may be diluted by the end user. Alternatively, the solution may be prepared in dilute form, for example, from about 0.05 to about 8 wt %, and more typically, from about 0.016 to about 4, 3, 2, or 1 wt %.

Solutions having from about 0.5 to about 1.0 wt % hydrogen peroxide are suitable for use as household and commercial disinfectants, bactericides, virucides, sanitizers and cleaners. Solutions having from about 3 to about 4 wt % are suitable for use as multipurpose cleaners and bleach alternatives in healthcare facilities, households and commercial facilities. Solutions having from about 6 to about 8 wt % hydrogen peroxide are suitable for use as sporicides, fungicides, virucides, bactericides, broad spectrum sanitizers, general purpose cleaners, and each alternatives particularly in institutional healthcare and food applications.

Solvents, including water soluble solvents and water dispersible solvents can be added to inventive compositions to enhance cleaning and germicidal activity. For example, a short-chain alcohol, e.g., a $C_{1-6}$ alcohol, especially methanol, ethanol, or isopropanol may be added to provide additional cleaning ability for organic contaminates. Typically, the amount of short-chain alcohol in inventive compositions ranges from about 0.1 to about 10 wt % of the composition. Similarly, benzyl alcohol may also be used for the same purpose. Such alcohols are particularly suitable for use in ready-to-use formulations.

By comparison, glycol ethers are well-suited for use in concentrated formulations that may be diluted prior to use. For example, the use of glycol ethers in inventive compositions provide additional advantages, such as streak-free properties, added stability and better efficacy. Exemplary glycol ethers for use in the present invention include propylene glycol propyl ether, ethylene glycol butyl ether, ethylene glycol n-hexyl ether, propylene glycol methyl ether, hexylene glycol ethyl ether, propylene glycol butyl ether, carbitol, or mixtures of two or more thereof. Typically, glycol ethers may be present at amounts of from about 0.1 to about 30 wt % of the compositions.

Compositions of the invention may include surfactants including nonionic, anionic, cationic or amphoteric surfactants. Anionic surfactants suitable for use in the present invention include sulfonic acids, sulfates, alkali metal and ammonium salts thereof and mixtures thereof. In particular, anionic surfactants include $C_{8-16}$-alkyl aryl sulfonic acids and alkali metal and ammonium salts thereof, sulfonated $C_{12-22}$ carboxylic acids and alkali metal and ammonium salts thereof, $C_{8-22}$-alkyl diphenyl oxide sulfonic acids and alkali metal and ammonium salts thereof, naphthalene sulfonic acids and alkali metal and ammonium salts thereof, $C_{8-22}$ alkyl sulfonic acids and alkali metal and ammonium salts thereof, alkali metal $C_{8-18}$ alkyl sulfates, and mixtures thereof, in a concentration range of from 0.02 to 15 wt % of the solution. Typically, the anionic surfactant is an alkyl aryl sulfonate, especially a $C_{10-16}$ alkyl benzene sulfonate or mixtures thereof. Dodecyl benzene sulfonate, and tridecyl benzene sulfonate and their salts, e.g. sodium, potassium, ammonium salts are especially useful anionic surfactants. Other exemplary anionic surfactants include sulfonated 9-octadecanoic acid, diphenyl oxide sulfonic acids and salts, dodecyl diphenyl oxide disulfonic acid and disodium 4-dodecylated diphenyloxide sulfonate, alkylated sulfonated diphenyl oxide disodium salt, the sodium salts of 1-octane sulfonic acid, 1-decane sulfonic acid and tridecane sulfonic acid and sodium lauryl sulfate.

Nonionic surfactants can also be added to inventive compositions to improve cleaning while retaining or improving antimicrobial activity. Although a number of emulsifiers such as alkyl phenoxypolyethoxy ethanol or polyoxyethylene surfactants are beneficial for cleaning surfaces of organic matter or grease, it has been found that shorter chain polyoxyethylene, $C_6$ to $C_{10}$ nonionic surfactants provide superior cleaning ability. Thus, for example, LUTENSOL ON 30 C10 (synthetic C1O oxoalcohol) and the like may be used. Another example is Alfonic L 610-3.5 (C5-C10 ethoxylated 3.5 mol of EO from Sasol Chemicals. Other useful nonionic surfactants such as include block copolymers such as phosphate esters such as Novell (C6/EO2 PO from Sasol Chemicals), Pluronic L43 (block copolymer of PO/EO from BASF) and phosphate esters such as ANTARA LP-700 (polyoxyethylene phenyl ether phosphate from Rhodia). Likewise, amine oxides are also useful in inventive compositions. For example, Malkamine C8 amine oxide (octyl amine oxine from McIntyre) Amphoteric surfactants, such as cocamphodipropionate and caprylamphodiproprionate, are also suitable for us in the present invention.

Inventive compositions can include chelating agents and sequestrants. Exemplary agents include ethylenediaminetetraacetric acid (EDTA), diaethylenetriaminepentaacetic acid (DTPA), HEDTA, HEIDA or nitrilotriacetic acid (NTA), sucrose sequestrant (e.g., BEIXON AB-200%, Chtr-Beitlich less than 5%) or sodium acid pyrophosphate/1,3-diamino-2-hydroxypropane-4N tetraacetic acid. These chelating agents and sequestrants may be used with or without polyphosphonates such as 1-hydroxyethylidene-1,1-diphosphonic acid. The preferred range of the chelating agent is from 0.1% to 10%.

EXAMPLE 4

Using Various Surfactants

To a base formula (with no chelate), additions of the following ingredients are added and corrected for % water.

All test formulations were diluted 1/64 in 400 PPM (as $CaCO_2$) hard water containing 5.0% horse serum. The test material was held at ambient temperature (24° C.) for 60 seconds at which time a 0.1 ml portion of a 24 hr Brain Heart Infusion broth culture of S. aureus ATCC 6538 was added to the test solution and mixed. After 5 min at ambient temperature, the test solution was mixed and a 1.1 ml sample withdrawn and placed into 9.9 ml universal neutralizer. A 0.1 ml portion of test organism added to 9.9 ml of standard hard water containing 5% horse serum and enumerated after 5 minutes served as a control.

Universal neutralizer
RT
3 g lecithin
0.5 g fluid thioglycollate broth
1 g histidine
10 ml phosphate buffer
10 ml phosphate buffer 0.25 N
5 g Sodium thiosulphate
30 ml Tween
Bring volume to 1 L with di water The sample was serially diluted in universal neutralizer and the number of 15 surviving organism enumerated by pour plating with Microbial Content Test Agar. A plated were inverted and incubated at 32° C. for 48 hrs. Colonies were counted with the aide of Quebec colony counter and $\log_{10}$ reduction in colony forming units (CFU)/ml compared to CFU/ml of control samples was determined for each formulation.

Results are in the table below.

| Chemical | %/Wt | Reduction in $\log_{10}$ CFU/ml vs controls | 4 week hydrogen peroxide loss (50 C) |
|---|---|---|---|
| Cocoamphodipropionate | 3.0 | >5.56 | 26.92% |
| Cocoamphodipropionate | 5.0 | >5.56 | 38.13% |
| Caprylamphopropionate | 3.0 | >5.56 | 29.95% |
| Caprylamphopropionate | 5.0 | >5.56 | 44.42% |
| Alky dimethyl Benzyl Ammonium Chloride | 0.5 | >5.56 | 8.20% |
| Alky dimethyl Benzyl Ammonium Chloride | 3.0 | 2.99 | 59.35% |
| Lauroyl ethylene diamine triacetic acid | 0.5 | 3.30 | 0.79% |
| Lauroyl ethylene diamine triacetic acid | 1.0 | 3.14 | 9.55% |
| HEIDA (28%) | 0.5 | 5.81 | <1% |
| HEIDA (28%) | 2.0 | >5.56 | 6.59% |
| Lauryl Amine Oxide | 1.00 | >5.56 | 3.46% |
| Standard Formula | | >5.56 | 4.52% |

EXAMPLE 5

Improved Broad Anti-Microbiology of Neo-Acid

In this example a suspension efficacy test was run on several of the previous examples against *mycobacterium smegmatis*. The samples were tested both neat and at a 1:16 dilution Procedure:
Bacterial Preparation

*M. smegmatis* was grown at 37° C. on nutrient agar for 48 hrs. Three consecutive transfers were done with the last being the working culture. Two slants of the third transfer were harvested into 10 ml sterile DI water with 3 grams sterile glass beads. The culture was vortexed for 30 seconds. The cutlure was allowed to settle for 15 minutes before testing.

Test Solution

The experimental formulations were tested neat and at a 1:16 dilution. The 1:16 dilution was made in sterile 400 ppm hardwater (10 ml hardwater+0.625 uL experimental formulation).

Suspension Test Procedure

Ten (10) ml of test solution (either neat or the 1:16 dilution) was placed in a sterile tube. One hundred micro liters (100 uL) of working bacterial suspension was added to test solution. Solution was vortexed and timer started for 5 minutes. After 5 minutes, the solution was re-vortexed and 1.1 ml of solution was added to 9.9 ml of universal neutralizer. Serial dilutions were done from −1 to −4. The samples were pour plated using Nutrient Agar. The plates were incubated for 5 days at 37° C. The plates were counted and log reduction calculated. Testing was performed at ambient temperature.

The control was sterile water. Serial dilutions were done from −2 to −6.

Results

| SAMPLE | Log CFU/ml | Log reduction |
|---|---|---|
| CONTROL | 5.61 | NA |
| Example 4 with Phosphoric Acid @ 2.94% | | |
| neat | <1 | >4.61 |
| 1:16 | 5.05 | 0.56 |
| With hexylene glycol ether @ 1.5% in place of solvent | | |
| neat | <1 | >4.61 |
| 1:16 | 5.65 | −0.04 |
| Example 4 with DMPA @3.80% | | |
| neat | <1 | >4.61 |
| 1:16 | 2.48 | 3.13 |
| Example 4 with DMPA @ 6.5% | | |
| neat | <1 | >4.61 |
| 1:16 | 2.69 | 2.92 |
| Example 4 with Neo-Heptanoic @ 5.6% | | |
| neat | <1 | >4.61 |
| 1:16 | <1 | >4.61 |
| Example 4 with Neo-Nonanoic @7.25% | | |
| neat | <1 | >4.61 |
| 1:16 | <1 | >4.61 |
| Example 4 with Neo-Decanoic @8.25% | | |
| neat | <1 | >4.61 |
| 1:16 | <1 | >4.61 |
| Example 4 with Butyl Carbitol @ 10% in place of solvent | | |
| neat | <1 | >4.61 |
| 1:16 | 4.98 | 0.63 |

Several adjuvants may be added to the composition such as corrosion inhibitors like benzotriazole, methyl benzotriazole, fragrances and viscosity modifiers.

In accordance with another aspect of the invention, there is provided a composition comprising 3.5%-30% wt % hydrogen peroxide; 0.5-20% wt % of a carboxylic acid resistant to oxidation; 0.5-10% wt % of a nonionic surfactant; 0.05-5% wt % of a chelating agent or sequestrant; and 2-30% wt % of a solvent that is water soluble or water dispersible. The composition can also include 0.5-20% wt % of an anionic surfactant.

In another aspect, the present invention provides methods of cleaning and disinfecting a surface. The methods include applying a composition as described herein to the surface. Inventive compositions are particularly well suited for cleaning and disinfecting hard surfaces including, but not limited to, glass, metal, such as aluminum and stainless steel, porcelain, tile and grout, and other surfaces such as found in restrooms, kitchens and the like. Inventive compositions may be applied in ready-to-use formulations or may be diluted with water prior to applying to the surface to be cleaned. It is an advantage of the present compositions that a single concentrate may be diluted to various concentrations and retains antimicrobial activity at the various dilutions. For example, diluting of 1:4, 1:8, 1:16, 1:32, 1:64, 1:128 and 1:256 of disinfectant to water may be made. In addition, inventive compositions may be used to maintain grout and fixtures from either iron or hard water stains and may also be used to whiten grout.

EXAMPLE 6

Cleaning Results Obtained with Various Carboxylic Acids

Glass Cleaning results were done using a Modified CSMA DCC-09 for Glass Cleaner. A panel was used to evaluate the cleaning, wetting, streaking and residual wiping using glass mirrors with a scale of one to five, five being a good cleaner and 1 being a poor cleaner. The following results are an average of the composite results in the four categories. All examples were also run in 300 ppm hard water and diluted to 1:32.

| Material | Wt % | Wt % | Wt % | Wt % | Wt % | Glance HC* @1:40 |
|---|---|---|---|---|---|---|
| Deionized Water | 52.46 | 52.90 | 52.90 | 52.90 | 52.90 | |
| Phosphoric Acid | 2.94 | | | | | |
| Neo pentanoic acid, 100% | | 2.50 | | | | |
| Neo heptanoic acid, 100% | | | 2.5 | | | |
| Neo nonanoic acid, 100% | | | | 2.5 | | |
| Neo decanoic acid, 100% | | | | | 2.5 | |
| Dequest 2010 | 8.0 | 8.0 | 8.0 | 8.0 | 8.0 | |
| Biosoft S-101 | 5.0 | 5.0 | 5.0 | 5.0 | 5.0 | |
| Dowfax C-10L | 5.0 | 5.0 | 5.0 | 5.0 | 5.0 | |
| Downaol PnP | 10.0 | 10.0 | 10.0 | 10.0 | 10.0 | |
| Alfonic L610-3.5 | 1.5 | 1.5 | 1.5 | 1.5 | 1.5 | |

-continued

| Material | Wt % | Wt % | Wt % | Wt % | Wt % | Glance HC* @1:40 |
|---|---|---|---|---|---|---|
| Hydrogen Peroxide, 50% | 15.00 | 15.0 | 15.0 | 15.0 | 15.0 | |
| Benzotriazole | 0.10 | 0.1 | 0.10 | 0.10 | 0.10 | |
| Solution stability | Stable Clear | Stable clear | Stable clear | Stable clear | Stable clear | |
| Stability in Hard Water (400 ppm @ 1:64 | Slight haze | Slight haze | Slight haze | Clear | Clear | Slight Haze |
| % Loss of hydrogen peroxide in 4 weeks@ 50 C. | 5.68% | 19.15% | 11.36% | 6.24% | 6.09% | NA |
| Mirror Cleaning Performance: Average Cleaning Results | 3.15 | 3.33 | 2.98 | 2.83 | 2.64 | 3.06 |

Typically, inventive compositions are prepared simply by combining the hydrogen peroxide and the acid resistant to oxidation as well as any other ingredients that are desired. Generally, those ingredients can be added sequentially or all at once to form an aqueous solution. In some embodiments, the hydrogen peroxide is added last to the solution.

As will be understood by one skilled in the art, for any and all purposes, particularly in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub ranges as discussed above. All patents and publications described herein are incorporated by reference in their entirety for all purposes.

EXAMPLE 7

Low Phosphoric Levels

| Material | Wt % |
|---|---|
| Deionized Water | 61.275 |
| Phosphoric Acid | 0 |
| Neo nonanoic acid, 100% | 5.0 |
| Dow Fax C10L | 5.0 |
| Biosoft S-101 | 5.0 |
| Downaol PnP | 8.0 |
| Alfonic L610-3.5 | 3.0 |
| Dow HEIDA, 28% | 1.00 |
| Benzotriazole | 0.10 |
| Hydrogen Peroxide | 11.60 |
| 4 week H2O2 loss @ 50° C. | 6.67% |
| 4 week H2O2 loss @ room temp. | 1.20% |
| AOAC Use Dilution @ 1:16 Dilution 5 min. contact, 400 ppm hard water and 5% blood serum S. aureus | 0/30 |

What is claimed is:

1. A composition comprising:
   hydrogen peroxide;
   1-hydroxyethylene-1,1-diphosphonic acid;
   at least one anionic surfactant; and
   an acid selected from neononanoic acid and neodecanoic acid.

2. The composition of claim 1 further comprising a solvent.

3. The composition of claim 2 wherein the solvent is propylene glycol propyl ether, ethylene glycol butyl ether, ethylene glycol n-hexyl ether, propylene glycol methyl ether, hexylene glycol ethyl ether, propylene glycol butyl ether, carbitol, alcohols, or a mixture of two or more thereof.

4. The composition of claim 1 further comprising a nonionic, cationic or amphoteric surfactant.

5. The composition of claim 4 wherein the surfactant is an alkyl phenoxypolyethoxy ethanol, a polyoxyethylene, an amine oxide, a multi block copolymer, a phosphate ester, an ethoxylated carboxylate, or a mixture of two or more thereof.

6. The composition of claim 1 further comprising a chelating agent or sequestrant.

7. The composition of claim 6 wherein the chelating agent or sequestrant is N-(hydroxyethyl)ethylenediamine triacetic acid, a sucrose sequestrant, or sodium acid pyrophosphate/1,3-diamino-2-hydroxypropane-4N-tetraacetic acid.

8. A composition comprising
   8 wt % hydrogen peroxide;
   8 wt % 1-hydroxyethylene-1,1-diphosphonic acid;
   5 wt % of an acid selected from neononanoic acid and neodecanoic acid;
   3 wt % of a nonionic surfactant;
   0.1 wt % of a chelating agent or sequestrant; and
   8 wt % of a solvent that is water soluble or water dispersible.

9. The composition of claim 8 further comprising 8 wt % of an anionic surfactant.

10. A method of cleaning and disinfecting a surface comprising applying a composition of claim 1 to the surface.

11. The method of claim 10 further comprising diluting the composition with water prior to applying it to the surface.

12. A method of making the composition of claim 1 comprising combining the hydrogen peroxide, the 1-hydroxyethylene-1,1-diphosphonic acid, at least one anionic surfactant, and the acid selected from neononanoic acid and neodecanoic acid.

13. The composition of claim 1 wherein the composition is contained on a pre-saturated wipe.

14. The composition of claim 13 wherein the wipe consists of a non-woven product.

15. The composition of claim 13 wherein the wipe consists of a disposable paper product.

16. The composition of claim 13 wherein the wipe consists of a fabric.

17. The composition of claim 1, wherein at least one anionic surfactant is an alkyl aryl sulfonic acid.

* * * * *